United States Patent
Baker et al.

(10) Patent No.: US 9,909,415 B2
(45) Date of Patent: Mar. 6, 2018

(54) METHOD AND APPARATUS FOR ANALYZING MIXING OF A FLUID IN A CONDUIT

(71) Applicant: Cameron International Corporation, Houston, TX (US)

(72) Inventors: James M. Baker, Tunbridge Wells (GB); Stuart F. Wright, Battle East (GB); Gary M. Potten, Houston, TX (US)

(73) Assignee: Cameron International Corporation, Houston, TX (US)

( * ) Notice: Subject to any disclaimer, the term of this patent is extended or adjusted under 35 U.S.C. 154(b) by 152 days.

(21) Appl. No.: 14/947,348

(22) Filed: Nov. 20, 2015

(65) Prior Publication Data

US 2017/0145820 A1   May 25, 2017

(51) Int. Cl.
    *E21B 49/08*   (2006.01)
(52) U.S. Cl.
    CPC ................... *E21B 49/08* (2013.01)
(58) Field of Classification Search
    CPC ......... E21B 49/08; G01N 15/08; G06F 23/00; G06F 19/00; G06F 1/20; G06F 1/74
    See application file for complete search history.

(56) References Cited

U.S. PATENT DOCUMENTS

| | | | |
|---|---|---|---|
| 2,322,018 A * | 6/1943 | Huber | G01N 1/2035 137/599.13 |
| 4,307,620 A | 12/1981 | Jiskoot | |
| 4,488,570 A | 12/1984 | Jiskoot | |
| 4,856,344 A | 8/1989 | Hunt | |
| 5,453,693 A | 9/1995 | Sinclair et al. | |
| 5,501,099 A * | 3/1996 | Whorff | G01F 1/3209 73/29.01 |
| 5,737,277 A | 4/1998 | Priest | |
| 2004/0011139 A1 | 1/2004 | Daniel et al. | |
| 2004/0240311 A1 * | 12/2004 | Hashiba | B01F 3/188 366/101 |

(Continued)

FOREIGN PATENT DOCUMENTS

WO   2014140539 A1   9/2014

OTHER PUBLICATIONS

"JISKOOT(TM) Quality Systems: JetMix(R)," Brochure, two pages, published by Cameron International Corporation, Houston, Texas, dated 2011.

(Continued)

*Primary Examiner* — Francis Gray
(74) *Attorney, Agent, or Firm* — Eubanks PLLC

(57) ABSTRACT

An apparatus for mixing fluids within a conduit and monitoring performance of the mixing is provided. In one embodiment, the apparatus includes a conduit and a fluid mixer coupled to the conduit for mixing fluid flowing through a bore of the conduit. The apparatus also includes multiple sensors for measuring a characteristic of the fluid at different locations in the bore of the conduit downstream from the fluid mixer. A controller of the apparatus can monitor performance of the fluid mixer in mixing the fluid flowing through the bore of the conduit based on the measured characteristic of the fluid at the different locations in the bore of the conduit downstream from the fluid mixer. Additional systems, devices, and methods are also disclosed.

21 Claims, 5 Drawing Sheets

(56) References Cited

U.S. PATENT DOCUMENTS

| | | | |
|---|---|---|---|
| 2005/0273278 A1* | 12/2005 | Sprague | G01F 1/3209 |
| | | | 702/45 |
| 2007/0055464 A1* | 3/2007 | Gysling | G01F 1/666 |
| | | | 702/50 |
| 2008/0016968 A1 | 1/2008 | McCall et al. | |
| 2010/0273273 A1 | 10/2010 | Cross et al. | |
| 2010/0319921 A1 | 12/2010 | Eia et al. | |
| 2013/0276514 A1* | 10/2013 | Claudon | B01D 46/442 |
| | | | 73/28.04 |
| 2015/0298082 A1 | 10/2015 | Machuca et al. | |
| 2016/0108729 A1* | 4/2016 | Li | G01N 11/16 |
| | | | 702/12 |

OTHER PUBLICATIONS

"JISKOOT In-Line Sampling System," Brochure, four pages, published by Cameron International Corporation, Houston, Texas, dated 2013.

"JISKOOT CoJetix Sampling System," Brochure, four pages, published by Cameron International Corporation, Houston, Texas, dated 2013.

* cited by examiner

METHOD AND APPARATUS FOR ANALYZING MIXING OF A FLUID IN A CONDUIT

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

In order to meet consumer and industrial demand for natural resources, companies often invest significant amounts of time and money in finding and extracting oil, natural gas, and other subterranean resources from the earth. Particularly, once desired subterranean resources such as oil or natural gas are discovered, drilling and production systems are often used to access and extract the resources. These systems may be located onshore or offshore depending on the locations of the desired resources. Once extracted, the resources are often transported via pipelines to desired locations, such as refineries.

Pipelines often convey multiple fluids simultaneously. For instance, flowing oil, water, and gas can be present in different proportions at a given location in the pipeline. In such cases, the fluid is often referred to as a multiphase fluid that includes individual phases of oil, water, and gas. Particulates, such as sand or sediment, may also be carried by the multiphase fluid. The fluid traveling through the pipeline can be analyzed to determine characteristics of the fluid. Such analysis can be performed in situ at the pipeline or on samples collected from the pipeline for future analysis, such as in a laboratory. Determined characteristics of fluid flowing through the pipeline may be used in various manners, such as to facilitate custody transfer of hydrocarbon fluids, auditing, taxation, and quality management.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Embodiments of the present disclosure generally relate to analysis of fluid mixtures flowing through conduits. In certain embodiments, an apparatus includes a fluid mixer that agitates and mixes fluid that is flowing through a conduit. The mixed fluid can be sampled at multiple locations in the conduit and analyzed to measure a characteristic of interest of the fluid at the multiple locations. The measured characteristic for the fluid at one sample location can then be compared to the measured characteristic for the fluid at another sample location to determine mixing performance of the fluid mixer. In at least some instances, the mixing performance is then improved by adjusting a mixing parameter in response to the determined mixing performance.

Various refinements of the features noted above may exist in relation to various aspects of the present embodiments. Further features may also be incorporated in these various aspects. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of some embodiments without limitation to the claimed subject matter.

BRIEF DESCRIPTION OF THE DRAWINGS

These and other features, aspects, and advantages of certain embodiments will become better understood when the following detailed description is read with reference to the accompanying drawings in which like characters represent like parts throughout the drawings, wherein.

DETAILED DESCRIPTION OF SPECIFIC EMBODIMENTS

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not require any particular orientation of the components.

Figure 1:
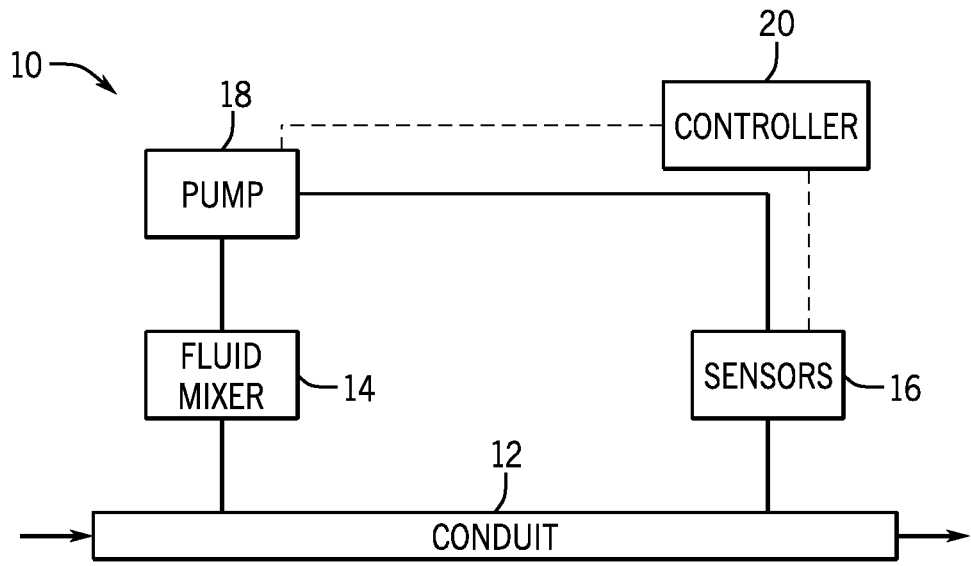
FIG. 1 is a block diagram representing components of an apparatus for conveying fluids through a conduit, mixing the fluids within the conduit, and analyzing mixing performance in accordance with certain embodiments of the present disclosure.

Turning now to the drawings, an apparatus 10 in which fluids can be mixed is generally illustrated in FIG. 1 by way of example. The apparatus 10 includes a fluid conduit 12, such as a pipeline. In at least some embodiments, a non-homogenous fluid (e.g., a multiphase fluid or a single-phase mixture of different fluids) is routed through the fluid conduit 12. The apparatus 10 includes a fluid mixer 14 for mixing components of the non-homogenous fluid together and one or more sensors 16 for analyzing the fluid routed through the conduit 12. In the presently depicted embodiment, the one or more sensors 16 analyze fluid from the conduit 12 after it is mixed by the fluid mixer 14.

A pump 18 is connected in fluid communication with the fluid mixer 14. In at least some embodiments, the pump 18 draws a portion of the fluid out of the conduit 12 and then pumps that drawn fluid back into the conduit 12 via the fluid mixer 14. The fluid returned through the fluid mixer 14 can be injected into the conduit 12 as fluid jets. These jets mix the fluid passing through the conduit 12. In other embodiments, the pump 18 draws a mixing fluid from some other source besides the conduit 12 (e.g., a fluid having a different grade than that flowing through the conduit 12 to the fluid mixer 14), and injects that other mixing fluid to mix the fluid flowing through the conduit 12.

Fluid in the conduit 12 downstream from the fluid mixer 14 can be sampled and analyzed via the sensors 16 to determine various fluid properties. Examples of such fluid properties include pressure, temperature, density, viscosity, flow rate, and phase proportions (e.g., water cut or oil cut). The sensors 16 are shown in series with the pump 18 in FIG. 1 as part of a return loop through which fluid is drawn from and then returned to the conduit 12, but one or more sensors 16 could also or instead be provided in parallel with the pump 18. Still further, in some embodiments one or more sensors 16 are positioned inside the bore of the conduit 12 (e.g., as part of a probe extending into the bore). Samples of fluid drawn from the conduit 12 could also be retained (e.g., in storage bottles) for later analysis.

Those skilled in the art will appreciate that multiphase fluids can flow through a pipeline under various flow regimes. For example, due to gravity, a multiphase fluid passing through a horizontal pipe may have a stratified flow in which, generally, water flows along the bottom of the pipe, oil flows through the pipe above the water, and gas flows over the oil in the top of the pipe. Sediment or other particulates can be carried by any of the individual phases but may be concentrated at the bottom of the pipe. In other instances, multiphase fluids can pass through a pipe in a different manner, such as in a plug flow, a slug flow, an annular flow, or a wavy flow.

In at least some embodiments, the pump 18 energizes a mixing fluid and injects that mixing fluid into the conduit 12 via the fluid mixer 14 to disrupt the flow pattern of the multiphase fluid and better mix its individual phases with one another. The mixer 14 can be used to mix two-phase flows (e.g., water and oil) in some embodiments, but could also be used to mix other multiphase flows (e.g., water, oil, and gas). This mixture can then be analyzed or sampled to determine characteristics of the multiphase fluid.

If the multiphase fluid were not sufficiently mixed, the composition of fluid at a particular location in the conduit 12 may not be representative of the composition of the multiphase fluid as a whole. As a result, measured characteristics based on the fluid at the particular location could be unreliable. For example, accuracy of sampling for the fraction of water contained within a water-in-oil mixture (i.e., the water cut) depends on adequate mixing. If water and oil flowing through a horizontal pipe were not well-mixed, fluid at the bottom of the pipe (e.g., fluid drawn from a sampling tap at the bottom of the pipe or analyzed in situ within the bottom of the pipe) at a given axial location along the pipe may have a higher proportion of water and a lower proportion of oil than is present at higher positions within the pipe at the given axial location. With mixing by the fluid mixer 14, however, the individual phases can be more evenly distributed within a cross-section of the conduit 12, which facilitates collection or analysis of a representative sample of the fluid mixture downstream from the mixing location.

Over-mixing of the fluid mixture, however, increases processing costs. A mixing system designed to continually mix a fluid at a rate that would ensure adequate mixing in a worst-case scenario for a given implementation (e.g., highest expected water density or salinity, lowest expected oil viscosity, and lowest expected oil density) would typically lead to over-mixing of the fluid at most process conditions. Further, sampling system performance can be validated occasionally (e.g., annually), such as with water injection proving tests. While such a test may verify a sufficient level of mixing at the time of the test, it does not ensure that the level of mixing is continually sufficient. Changes in fluid conditions and properties, for instance, could lead to insufficient mixing by the apparatus.

In accordance with certain embodiments of the present disclosure, the apparatus 10 uses an online measurement technique to monitor performance of the fluid mixer 14 in mixing fluid flowing through the bore of the conduit 12. In at least one embodiment, this online measurement technique includes measuring a characteristic of fluid at different locations in the bore of the conduit 12 downstream from the fluid mixer 14. These measurements can then be compared (e.g., via a controller 20) to determine mixing performance. The mixing performance may be continually monitored and used to confirm and log adequate mixing during sampling. In some instances, a mixing parameter could be adjusted based on the determined mixing performance. For example, if the mixing performance is determined to be lower than a desired threshold, the controller 20 could increase the operating speed of the pump 18 or activate additional mixing jets to increase the level of mixing. If the mixing performance is at or above the desired threshold, the mixing parameters could be adjusted (e.g., by lowering pump speed) to reduce over-mixing and online measurement of the mixing performance can be used to verify whether mixing performance remains at or above the desired threshold.

Figure 2:
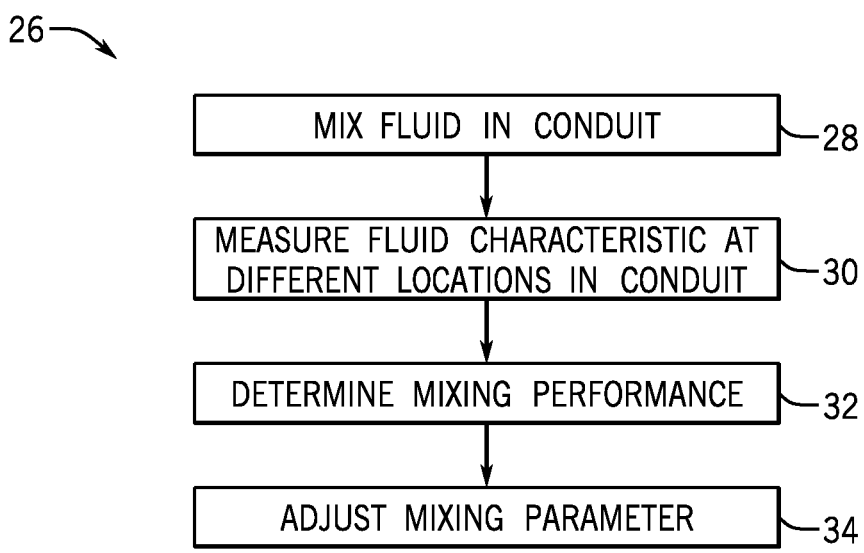
FIG. 2 is a flowchart representing a method for monitoring mixing performance of a fluid mixer based on a fluid characteristic measured for fluid at different locations within a conduit in accordance with one embodiment.

By way of example, a method for monitoring mixing performance is generally represented by the flowchart 26 of FIG. 2. The method includes mixing fluid in the conduit (block 28) with the fluid mixer 14. One or more fluid characteristics are then measured (block 30) at different locations in the bore of the conduit 12. For instance, a proportion of one or more components in the fluid mixture can be measured at different locations in the bore downstream from the fluid mixer 14. More specifically, in certain embodiments sensors 16 measure the proportions of water or oil phases in a multiphase fluid mixture at the different locations.

The mixing performance is then determined (block 32) based on the measured characteristic. For instance, the measurements of the characteristic (e.g., proportions of water or oil) at the different locations can be compared to one another to analyze homogeneity of the fluid mixture within the bore and sufficiency of the mixing. In some instances, the measured characteristic is used to derive a performance factor for the mixing. For example, and as described in greater detail below, a characteristic (e.g., water cut) of the fluid mixture can be measured at two different locations (e.g., within upper and lower portions of the bore of the conduit 12 at a given axial distance from the fluid mixer 14) and the ratio of the measurement at the two different locations can be used as an online performance factor for the mixing. The method represented in FIG. 2 further includes adjusting a mixing parameter (block 34), such as an operational characteristic of the pump 18, based on the determined mixing performance. In some instances, this includes optimizing mixing to ensure adequate mixing while minimizing over-mixing, such as described above. The adjustment of the mixing parameter may be performed dynamically (e.g., in real time) in response to the monitored mixing performance.

Figure 3:
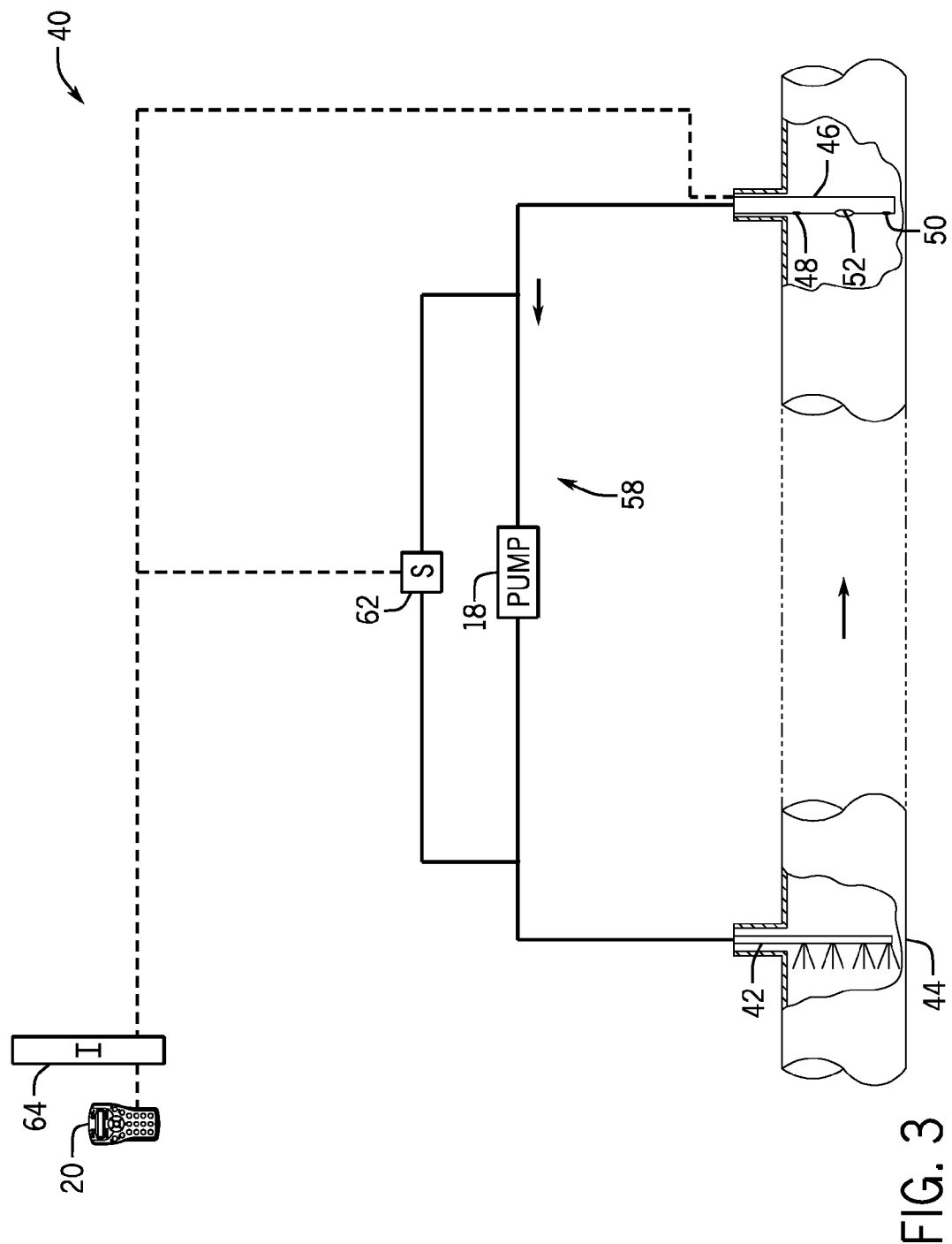
FIG. 3 generally depicts an apparatus for monitoring performance of a fluid mixer, the apparatus including a probe having sensors for measuring a characteristic of interest of a mixed fluid at different locations within a bore of a conduit, in accordance with one embodiment.
Figure 4:
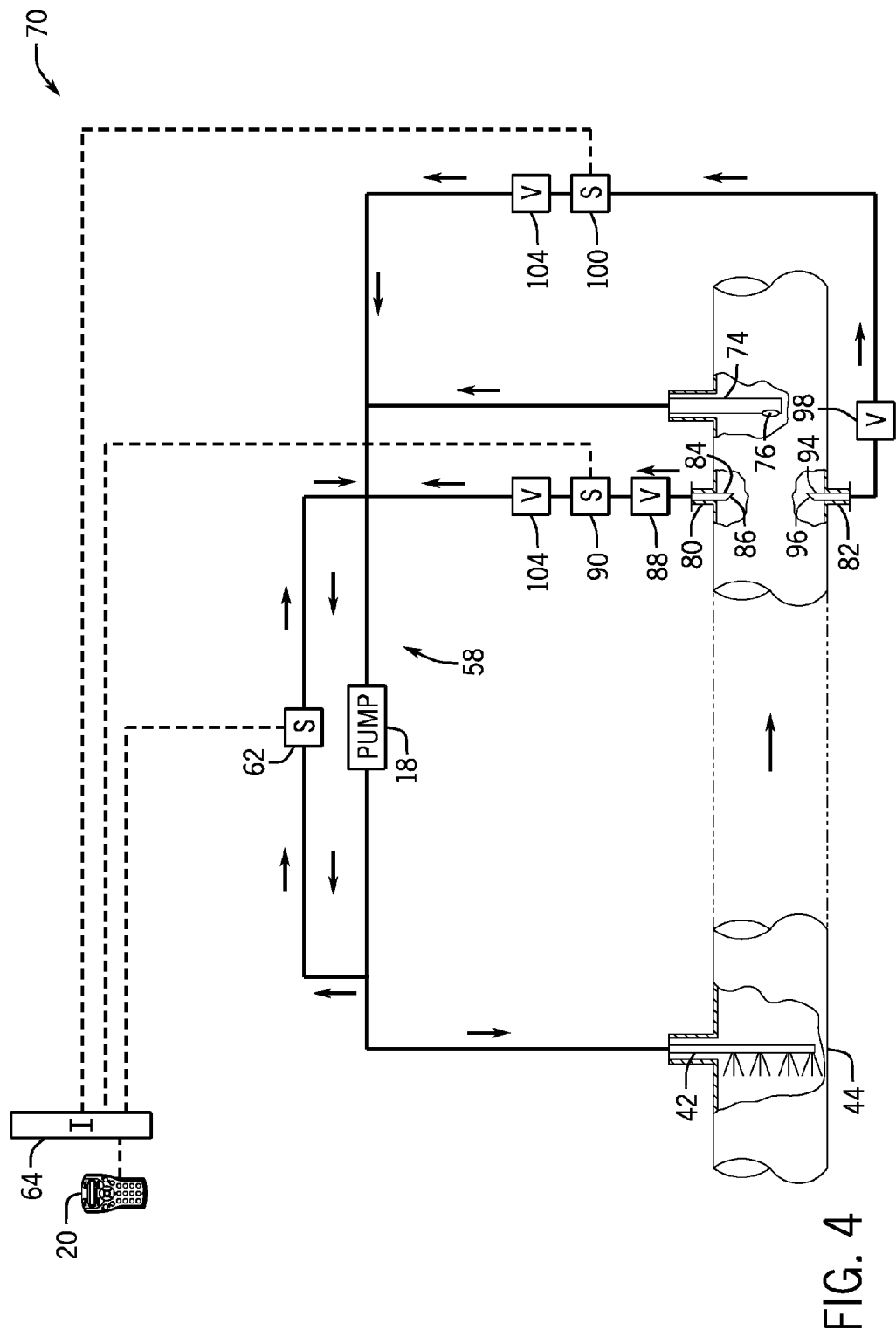
FIG. 4 generally depicts an apparatus for monitoring performance of a fluid mixer, the apparatus including multiple sampling taps for drawing fluid from multiple locations within the bore of the conduit and associated sensors for measuring a characteristic of interest for the fluid drawn via the sampling taps in accordance with one embodiment.
Figure 5:
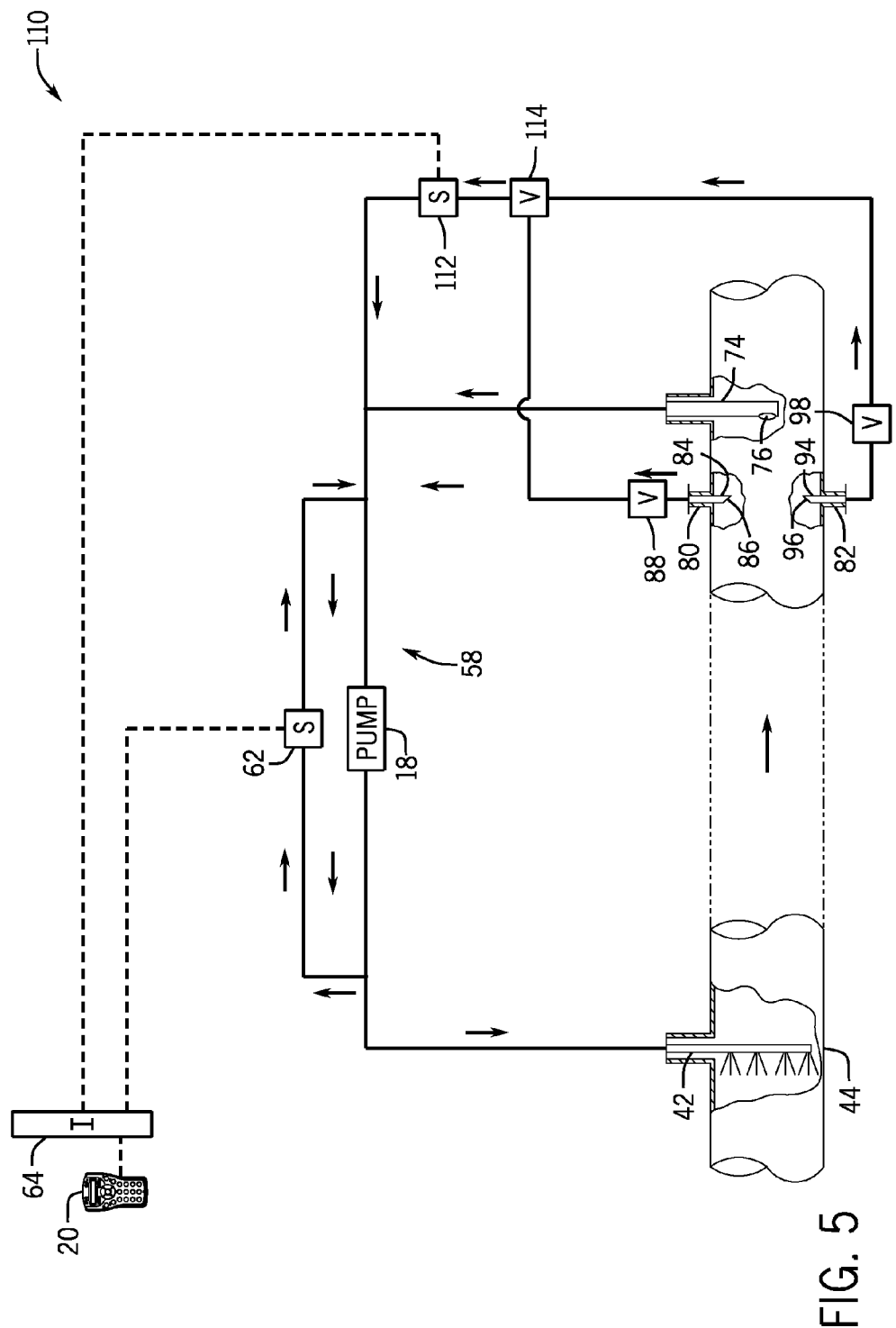
FIG. 5 generally depicts an apparatus similar to that of FIG. 4, but in which fluid from multiple sampling taps is routed to a shared sensor for analysis in accordance with one embodiment.

The apparatus 10 may be provided in any suitable configuration, certain examples of which are generally depicted in FIGS. 3-5. As shown in FIG. 3, the apparatus 10 is shown as a system 40 having a fluid mixer in the form of nozzle 42 extending into the bore of a conduit 44 (e.g., a pipeline). A mixing fluid is injected into the bore via the nozzle 42 to mix the fluid (e.g., a water-in-oil mixture or a stratified flow of oil and water) flowing through the conduit 44. While nozzle 42 is depicted as one example of a fluid mixer, it will be appreciated that the fluid mixer could be provided in some other form, such as a device that injects fluid into the bore directly through ports in the wall of the conduit 44 without a nozzle 42, or a rotor or other agitator moved within the bore to mix the fluids. In a further embodiment, multiple fluid mixers 14 may be installed in series in the conduit 44.

The mixed fluid flows downstream through the bore to a probe 46 extending into the bore. In the presently depicted embodiment, the probe 46 includes sensors 48 and 50 for sampling and measuring a characteristic of the fluid at two different locations within the bore. In at least some instances, the sensors 48 and 50 include sensors for measuring a composition characteristic of the sampled fluid (e.g., water-in-oil sensors for determining the water cut of the mixed fluid).

The probe 46 in FIG. 3 is provided as a quill having an inlet 52 for drawing a portion of the fluid from the conduit 44 into a return loop 58. The pump 18 controls flow of the drawn fluid through the return loop 58, and drawn fluid can be pumped back into the conduit 44 through the nozzle 42 to mix the fluid flowing through the bore. The return loop 58 is depicted as including an additional sensor 62 (e.g., a water-in-oil sensor) for measuring a characteristic (e.g., water cut) of the drawn fluid. Although the sensor 62 is not positioned inside the bore, it will be appreciated that the sensor 62 measures a characteristic of the fluid drawn from a particular location in the bore (i.e., at the inlet 52). Consequently, each of sensors 48, 50, and 62 can be said to measure a characteristic of the fluid at a different location within the bore. The sensors 48, 50, and 62 can transmit measurement data to the controller 20 directly or, as shown in FIG. 3, via a terminal interface 64. The measurements obtained with sensors 48, 50, and 62 can be compared (e.g., by the controller 20) to determine mixing performance.

In the embodiment depicted in FIG. 3, the sensors 48, 50, and 62 measure the characteristic at the same axial location in the bore of the conduit 44 downstream from the nozzle 42, but at different positions within a cross-section of the bore. More particularly, the inlet 52 is positioned at or near the central axis of the conduit 44, while the sensors 48 and 50 are positioned further from the central axis in opposite regions of the bore (e.g., upper and lower regions in the case of a horizontal conduit 44, though it is noted that the present technique could also be used with a vertical conduit 44). If the fluid flowing through the conduit 44 is mixed into a homogenous fluid mixture, the magnitude of the characteristic measured by the sensors 48, 50, and 62 should be substantially equal across the three sample locations in the bore. In contrast, measurements from sensors 48, 50, and 62 that meaningfully differ (e.g., outside a margin of measurement error or outside a desired range of variation) are indicative of non-homogeneity of the mixture and lower mixing performance.

In one embodiment, the sensors 48 and 50 are water-in-oil sensors and the ratio of the water cut measurement from sensor 48 to the water cut measurement from sensor 50 is calculated by the controller 20 as an online performance factor indicative of real-time mixing performance. In such an embodiment, a ratio equal to one is indicative of even dispersal of water throughout the bore and better mixing performance, while ratios further from one (e.g., approaching zero or infinity) indicate uneven dispersal of water throughout the bore and worse mixing performance. The sensor 62 can also be a water-in-oil sensor, and the water cut measured with sensor 62 could also be used with one or both of the measurements from sensors 48 and 50 in analyzing fluid mixture homogeneity and mixing performance. For instance, in one embodiment the three sensors are used to determine a water fraction profile across the bore section, and this profile is then used to confirm and log adequate mixing during sampling.

In one embodiment, the controller 20 adjusts mixing performance by controlling the operating speed of the pump 18. If the mixing performance is worse than desired (e.g., if the performance factor falls outside a desired range), the controller 20 can command an increase in the operating speed of the pump 18 to increase mixing of the flowing fluid via the nozzle 42. Similarly, the controller 20 can command a decrease in the operating speed of the pump 18 to avoid over-mixing, while continual monitoring of the mixing performance can be used to ensure a desired level of mixing is maintained. In other embodiments, the controller 20 can alter some other parameter of the mixing process. For instance, the flow rate of the fluid through the conduit 44 could be adjusted or, in an embodiment having multiple fluid mixers, the number of operating fluid mixers could be changed.

While the fluid characteristic of interest can be measured at different locations in the bore with a probe having multiple sensors, additional sampling taps in the conduit 44 could also or instead be used to measure the fluid characteristic at different locations within the bore. One example of an apparatus 10 having such sampling taps is generally depicted as system 70 in FIG. 4. In this depicted embodiment, the system 70 includes a probe 74 that extends into the bore of the conduit 44 downstream of a nozzle 42. Like the probe 46 of FIG. 3, the probe 74 is provided as a quill having an inlet 76 for drawing a portion of the fluid from the conduit 44 into a return loop 58 including the pump 18 and sensor 62.

The system 70 includes sampling taps 80 and 82 for sampling fluid from other locations within the bore of the conduit 44. The sampling tap 80 has a probe 84 with an inlet 86. In operation, the probe 84 samples fluid from within the bore of the conduit 44 at the inlet 86. With valve 88 open, the sampled fluid drawn via tap 80 can be analyzed with a sensor 90 to determine a characteristic of interest (e.g., water cut) for the fluid sampled from the bore at the location of the inlet 86. Similarly, the sampling tap 82 includes a probe 94 with an inlet 96 for sampling fluid from within the bore of the conduit 44 at the location of the inlet 96. The fluid drawn via the inlet 96 can be routed through valve 98 and analyzed with a sensor 100 to determine the characteristic of interest (e.g., water cut). In other instances, the probes 84 and 94 may be provided as in-line sensor probes (e.g., with sensors 90 and 100 integrated into the probes). And in yet another embodiment, one or more sensors (e.g., sensors 90 and 100) are embedded in the wall of the conduit 44. In the presently depicted embodiment, the probes 84 and 94 sample fluid from two different locations (e.g., in opposite sides of the bore) at the same axial position downstream of the mixing nozzle 42. And while the probe 74 is shown here to be axially offset from the probes 84 and 94, in other embodiments each of these probes may be aligned with one another in the same axial cross-section through the conduit 42 (e.g., with the probe 74 extending transversely into the bore between the inlets 86 and 96).

The sensor 62 can also be used to analyze fluid and determine the characteristic of interest. For example, valves 104 can be selectively closed to isolate the sampling taps 80 and 82 from the fluid drawn into the return loop 58 from the probe 74, allowing the sensor 62 to measure the characteristic of interest for the fluid sampled at the inlet 76. Valves 104 could be opened to allow the fluid to drawn through the taps 80 and 82 to be commingled with the fluid drawn via the probe 74 within the return loop 58. Like the sensors of FIG. 3, the sensors 62, 90, and 100 (e.g., water-in-oil sensors) of FIG. 4 can transmit measurement data to the controller 20 directly or via the terminal interface 64. And as also noted above, the characteristic of interest measured for fluid drawn from different locations in the bore can be compared to determine mixing performance of the fluid mixer upstream from the sampling locations.

While system 70 includes separate sensors for analyzing fluid from each of the sampling taps 80 and 82, fluid from the sampling taps 80 and 82 is routed to a shared sensor for analysis in other embodiments. One example of such an arrangement is generally depicted in FIG. 5 as system 110. Rather than having separate sensors 90 and 100, fluid drawn from the sampling taps 80 and 82 of the system 110 is routed to a shared sensor 112 (e.g., a water-in-oil sensor) for measuring the characteristic of interest. A selection valve 114 controls which sampled fluid (i.e., from tap 80 or 82) is routed to the sensor 112 and can be operated to route fluid from each of taps 80 and 82 at different times for analysis. The measurements taken by sensor 112 can be compared to each other or to those taken by sensor 62 to measure mixing performance.

Figure 6:
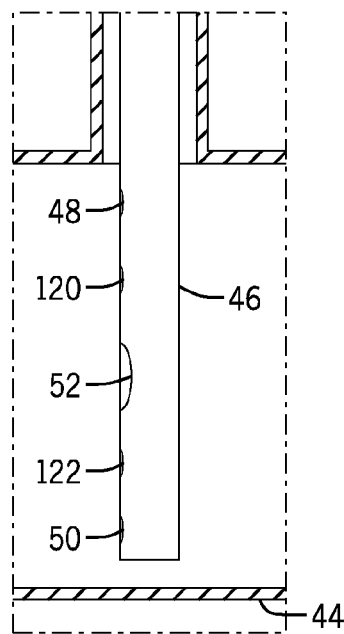
FIG. 6 is a detail view of a probe that can be used for sampling and analyzing fluid at multiple locations in the bore of a conduit in accordance with one embodiment.

Certain examples have been described above as using a measured characteristic of fluid samples drawn from three different locations within the bore of a conduit, but it will be appreciated that fluid could be drawn from some other number of different locations within the bore for analysis and use in determining mixing performance. For example, in some embodiments the water cut or other measured characteristic of fluid sampled from two locations within the bore (e.g., at sensors 48 and 50 of FIG. 2 or at inlets 86 and 96 in FIGS. 3 and 4) are compared to each other to determine mixing performance. In other embodiments, the characteristic of interest is measured for fluid at more than three locations within the bore. By way of example, a sampling probe 46 (or probe 74) could include additional sensors for measuring the characteristic of interest at other locations within the bore of the conduit 44. As depicted in FIG. 6, the sampling probe 46 includes not only inlet 52 and sensors 48 and 50 for measuring a characteristic of interest at three locations within the bore, but also includes additional sensors 120 and 122 for measuring the characteristic of interest at two additional locations. In at least one embodiment, the sensors 120 and 122 are identical to sensors 48 and 50. Any or all of the measurements of the characteristic of interest for the fluid sampled from different locations within the bore can be compared to one another to measure mixing performance.

Figure 7:
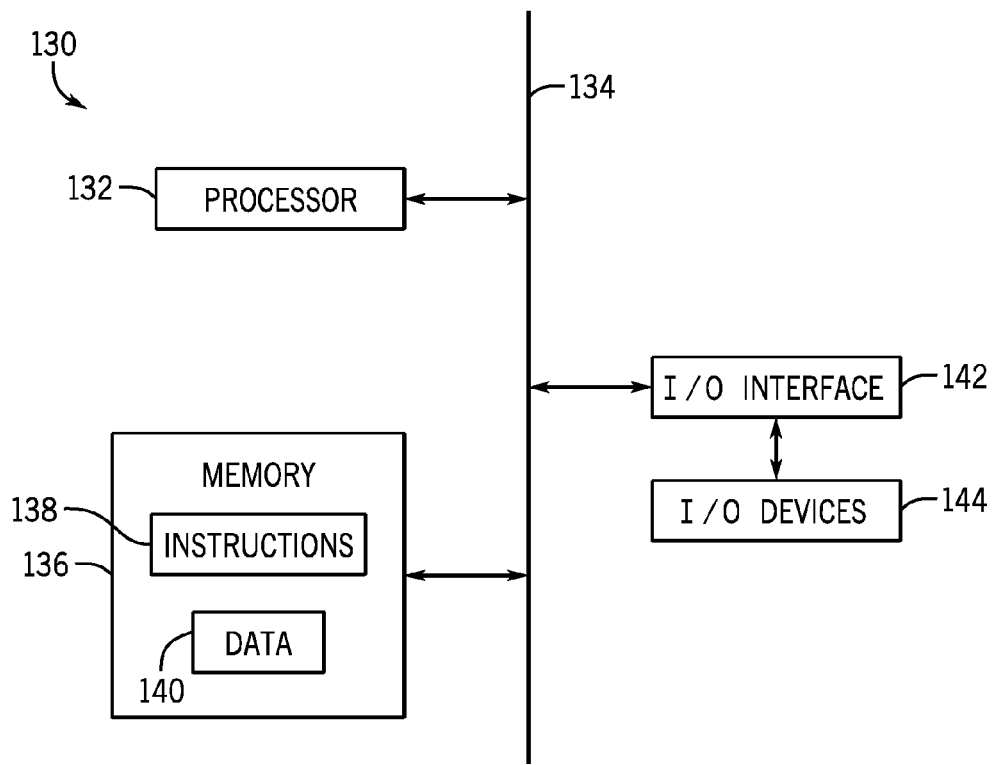
FIG. 7 is a block diagram of a programmable control system that can be used to monitor and adjust mixing performance of a fluid mixer in accordance with one embodiment.

Finally, it is noted that the control system or controller 20 for implementing various functionality described above can be provided in any suitable form. In at least some embodiments, the controller 20 is provided in the form of a processor-based system, an example of which is provided in FIG. 7 and generally denoted by reference numeral 130. In this depicted embodiment, the system 130 includes a processor 132 connected by a bus 134 to a memory device 136. It will be appreciated that the system 130 could also include multiple processors or memory devices, and that such memory devices can include volatile memory (e.g., random-access memory) or non-volatile memory (e.g., flash memory and a read-only memory).

The one or more memory devices 136 are encoded with application instructions 138 (e.g., software executable by the processor 132 to perform various functionality described above) and data 140. For example, in one embodiment the application instructions 138 can be executed to monitor mixing performance via a measured characteristic of fluid sampled from different locations in the bore and to dynamically adjust mixing of fluids (e.g., of water and oil) in a conduit by the fluid mixer based on the monitored mixing performance. In one embodiment, the application instructions 138 are stored in a read-only memory and the data 140 is stored in a writeable non-volatile memory (e.g., a flash memory).

The system 130 also includes an interface 142 that enables communication between the processor 132 and various input or output devices 144. The interface 142 can include any suitable device that enables such communication, such as a modem or a serial port. The input and output devices 144 can include any number of suitable devices. For example, in one embodiment the devices 144 include the sensors for measuring the characteristic of interest in the sampled fluid and devices controlled by the system 130 (e.g., the pump 18) to alter a mixing parameter. The devices 144 can also include a keyboard, buttons, or a touchscreen to allow user-input to the system 130, and a display or printer to output information from the system 130 to a user.

While the aspects of the present disclosure may be susceptible to various modifications and alternative forms, specific embodiments have been shown by way of example in the drawings and have been described in detail herein. But it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus comprising:
a conduit having a bore;
a fluid mixer coupled to the conduit for mixing fluid flowing through the bore of the conduit;
a plurality of sensors for measuring a characteristic of the fluid at different locations in the bore of the conduit downstream from the fluid mixer; and
a controller operable to monitor performance of the fluid mixer in mixing the fluid flowing through the bore of the conduit based on the measured characteristic of the fluid at the different locations in the bore of the conduit downstream from the fluid mixer;
wherein the plurality of sensors for measuring the characteristic includes a plurality of sensors for measuring a proportion of one or more phases in a multiphase fluid, the multiphase fluid includes water and oil, and the plurality of sensors for measuring the proportion of one or more phases in the multiphase fluid includes a plurality of sensors for measuring a proportion of the water or oil of the multiphase fluid at the different locations in the bore.

2. The apparatus of claim 1, wherein the controller is operable to monitor performance of the fluid mixer in mixing the fluid flowing through the bore of the conduit through comparison of the proportions of the water or oil of the multiphase fluid at the different locations in the bore.

3. The apparatus of claim 1, comprising a probe having at least two sensors of the plurality of sensors, wherein the probe extends into the bore of the conduit such that the at least two of the plurality of sensors are positioned within the bore of the conduit.

4. The apparatus of claim 1, wherein the plurality of sensors for measuring the characteristic of the fluid at the different locations in the bore of the conduit downstream from the fluid mixer includes a plurality of sensors for measuring the characteristic of the fluid at three or more different locations in the bore of the conduit downstream from the fluid mixer.

5. The apparatus of claim 4, wherein at least two of the three or more different locations in the bore of the conduit downstream from the fluid mixer are at the same axial position within the bore.

6. The apparatus of claim 1, wherein the conduit includes separate taps for sampling portions of the multiphase fluid from at least two of the different locations in the bore of the conduit downstream from the fluid mixer and routing the sampled portions to one or more sensors of the plurality of sensors.

7. The apparatus of claim 1, wherein the fluid mixer is configured to inject a mixing fluid into the bore of the conduit to mix the fluid flowing through the bore.

8. The apparatus of claim 7, wherein the fluid mixer includes a nozzle inside the bore of the conduit for injecting the mixing fluid into the bore.

9. The apparatus of claim 7, comprising a pump configured to pump the mixing fluid into the bore of the conduit, wherein the controller is operable to control an operating characteristic of the pump based on measured performance of the fluid mixer in mixing the fluid flowing through the bore.

10. The apparatus of claim 9, wherein the pump is coupled to draw the mixing fluid from the bore and then reintroduce the mixing fluid, via the fluid mixer, into the bore.

11. An apparatus comprising:
a probe configured to be installed in a pipeline such that the probe extends into a bore of the pipeline, wherein the probe includes:
a first sensor for measuring a composition characteristic of a fluid at a first location in the bore of the pipeline; and
a second sensor for measuring the composition characteristic of the fluid at a second location in the bore of the pipeline; and
a controller configured to receive the measured composition characteristic of the fluid at the first and second locations and to use the measured composition characteristic at the first and second locations to analyze homogeneity of the fluid within the bore.

12. The apparatus of claim 11, wherein the probe is installed in the pipeline, the apparatus includes a fluid mixer coupled to the pipeline upstream of the probe, and the controller is configured to measure performance of the fluid mixer via the measured composition characteristic at the first and second locations.

13. A method comprising:
measuring a water cut or oil cut of a multiphase fluid having water and oil flowing through a bore of a conduit at a first position within the bore;
measuring the water cut or oil cut of the multiphase fluid flowing through the bore of the conduit at a second position within the bore; and
determining performance of a fluid mixer positioned upstream of the first and second positions based on the measured water cut or oil cut at the first and second positions.

14. The method of claim 13, comprising dynamically adjusting mixing of water and oil flowing through the bore with the fluid mixer based on the measured water cut or oil cut of the multiphase fluid at the first and second positions.

15. The method of claim 13, comprising measuring the water cut or oil cut of the multiphase fluid flowing through the bore of the conduit at a third position within the bore.

16. The method of claim 15, wherein the third position within the bore is radially closer to the center of the bore than are the first and second positions.

17. The method of claim 15, wherein measuring the water cut or oil cut of the multiphase fluid flowing through the bore of the conduit at the third position within the bore includes drawing a sample of the multiphase fluid at the third position out of the bore through a probe extending into the bore and then measuring the water cut or oil cut of the sample.

18. The method of claim 17, wherein measuring the water cut or oil cut of the multiphase fluid flowing through the bore of the conduit at the first and second positions within the bore includes measuring the water cut or oil cut of the multiphase fluid flowing through the bore of the conduit at the first and second positions with sensors of the probe extending into the bore.

19. An apparatus comprising:
a conduit having a bore;
a fluid mixer coupled to the conduit for mixing fluid flowing through the bore of the conduit;
a plurality of sensors for measuring a characteristic of the fluid at different locations in the bore of the conduit downstream from the fluid mixer;
a controller operable to monitor performance of the fluid mixer in mixing the fluid flowing through the bore of the conduit based on the measured characteristic of the fluid at the different locations in the bore of the conduit downstream from the fluid mixer; and a probe having at least two sensors of the plurality of sensors, wherein the probe extends into the bore of the conduit such that the at least two of the plurality of sensors are positioned within the bore of the conduit.

20. An apparatus comprising:
a conduit having a bore;
a fluid mixer coupled to the conduit for mixing fluid flowing through the bore of the conduit;
a plurality of sensors for measuring a characteristic of the fluid at different locations in the bore of the conduit downstream from the fluid mixer, wherein the plurality of sensors for measuring the characteristic of the fluid at the different locations in the bore of the conduit downstream from the fluid mixer includes a plurality of sensors for measuring the characteristic of the fluid at three or more different locations in the bore of the conduit downstream from the fluid mixer; and
a controller operable to monitor performance of the fluid mixer in mixing the fluid flowing through the bore of the conduit based on the measured characteristic of the fluid at the different locations in the bore of the conduit downstream from the fluid mixer.

21. An apparatus comprising:
a conduit having a bore;
a fluid mixer coupled to the conduit for mixing fluid flowing through the bore of the conduit;
a plurality of sensors for measuring a characteristic of the fluid at different locations in the bore of the conduit downstream from the fluid mixer; and
a controller operable to monitor performance of the fluid mixer in mixing the fluid flowing through the bore of the conduit based on the measured characteristic of the fluid at the different locations in the bore of the conduit downstream from the fluid mixer;
wherein the fluid mixer is configured to inject a mixing fluid into the bore of the conduit to mix the fluid flowing through the bore, the apparatus also comprises a pump configured to pump the mixing fluid into the bore of the conduit, and the controller is operable to control an operating characteristic of the pump based on measured performance of the fluid mixer in mixing the fluid flowing through the bore.

* * * * *